United States Patent [19]

Goetz et al.

[11] Patent Number: 4,920,232
[45] Date of Patent: Apr. 24, 1990

[54] α,β-SUBSTITUTED ACROLEINS

[75] Inventors: Norbert Goetz, Worms; Stefan Karbach; Hans-Gert Recker, both of Ludwigshafen, all of Fed. Rep. of Germany

[73] Assignee: BASF Aktiengesellschaft, Ludwigshafen, Fed. Rep. of Germany

[21] Appl. No.: 211,838

[22] Filed: Jun. 27, 1988

[30] Foreign Application Priority Data

Jul. 10, 1987 [DE] Fed. Rep. of Germany ....... 3722886

[51] Int. Cl.$^5$ .................. C07D 213/56; C07D 213/46; C07D 211/30; C07D 315/00
[52] U.S. Cl. .................... 546/338; 546/246; 546/248; 546/340; 544/224; 544/335; 548/204; 548/236; 548/240; 549/13; 549/426; 549/427; 549/496; 549/498; 549/77; 549/78
[58] Field of Search ................................ 546/340, 338

[56] References Cited

FOREIGN PATENT DOCUMENTS 2516623 10/1975 Fed. Rep. of Germany ...... 546/334
1206903 9/1970 United Kingdom ................ 546/334

OTHER PUBLICATIONS

Houben-Weyl, Methoden der Organischen Chemie, vol. VII/1, 76 et seq.
Annalen der Chemie, 586 (1954), 110.
A. T. Nielsen and W. J. Houlihar, Organic Reactions, 16 (1968), 15 et seq.
Journal Praktische Chemie, 90 (1912), 227 et seq.
Chemische Berichte, 85 (1952), 1116 et seq.

*Primary Examiner*—Mary C. Lee
*Assistant Examiner*—J. Richter
*Attorney, Agent, or Firm*—John H. Shurtleff

[57] ABSTRACT

Known and novel substituted acroleins of the general formula I

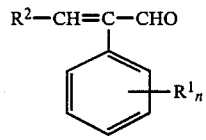

where $R^1$ is alkoxy, phenoxy, halogen, haloalkyl, haloalkoxy, haloalkylthiyl or nitro, n is an integer from 1 to 5, in the case of n being greater than 1 the $R^1$s being identical or different and in the event of nitro substitution the aromatic ring carrying not more than 3 nitro groups, and where $R^2$ is alkyl, cycloalkyl, unsubstituted or substituted aryl or hetaryl or a nonaromatic heterocyclic radical, are prepared by reacting a phenylacetaldehyde of the general formula II

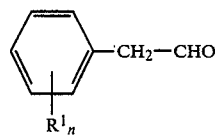

with an aldehyde of the general formula III

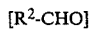

in the presence of a base and a solvent. These acroleins are useful to prepare hydroxymethyloxiranes which are intermediates in the synthesis of antimycotic and fungicidal azoylmethyloxiranes.

4 Claims, No Drawings

α,β-SUBSTITUTED ACROLEINS

The present invention relates to a process for preparing α,β-substituted acroleins of the general formula

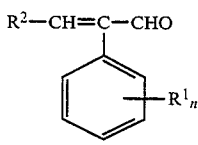   I where $R^1$ is alkoxy, phenoxy, halogen, haloalkyl, haloalkoxy, haloalkylthiyl or nitro, n is an integer from 1 to 5, in the case of n being greater than 1 the $R^1$s being identical or different and in the event of nitro substitution the aromatic ring carrying not more than 3 nitro groups, and where $R^2$ is alkyl, cycloalkyl, unsubstituted or substituted aryl or hetaryl or a nonaromatic heterocyclic radical.

The invention relates furthermore to novel α,β-substituted acroleins of the general formula Ia

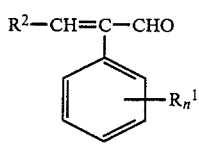   Ia where $R^1$ is halogen, $C_1$–$C_4$-alkoxy, phenoxy, $C_1$–$C_4$-haloalkyl, $C_1$–$C_4$-haloalkoxy or nitro, n is an integer from 1 to 5, in the case of n being greater than 1 the $R^1$s being identical or different and in the event of nitro substitution the aromatic ring carrying not more than 3 nitro groups, and where $R^2$ is a hetaromatic or nonaromatic heterocyclic radical containing from 1 to 3 nitrogen, oxygen and/or sulfur atoms.

It is known that crossed aldol condensations, depending on the structure and reactivity of the aldehydes used, frequently lead to product mixtures of varying compositious frequently coupled with low yields (Houben-Weyl, Methoden der organischen Chemie, vol. VII/1, 76 et seq.).

For instance, Alder (Ann. Chem. 586 (1954), 110) obtained α-phenylcinnamaldehyde from phenylacetaldehyde and benzaldehyde under basic condensation conditions in only moderate yields (69%).

In the reaction of phenylacetaldehyde with isovaleraldehyde under basic conditions the desired aldol product 5-methyl-2-phenylhex-2-enal can be isolated after fractional distillation in only very small yields of 16.5% (DE-A 1,921,560). The required purification and separation of such product mixtures is evidently problematic and extremely expensive; mixed aldol condensations are thus of little industrial interest (A. T. Nielsen and W. J. Houlihar, Org. Reactions 16 (1968), 15 et seq.; Houben-Weyl VII/I, 79).

From work by H. Stobbe and A. Lippold (J. Prakt. Chem. 90 (1912), 277 et seq.) we also know about the high high tendency of phenylacetaldehyde to self-condensation in the presence of acids or bases. The observations by W. Triebs and K. Krumbholz (Chem. Ber. 85 (1952), 1116 et seq.) concerning the spontaneous polymerization of phenylacetaldehyde under acidic or basic conditions confirm the existence of problems in handling this class of substances.

It is an object of the present invention to prepare specifically substituted acroleins having a phenyl radical in the 2-position which shall be additionally substituted, in particular by electron-withdrawing radicals. The synthesis shall start from readily available starting materials, give good yields, high chemical selectivity and products which are easy to isolate, and hence be suitable for trouble-free operation in industry.

We have found that this object is achieved with a process for preparing an α,β-substituted acrolein of the general formula I

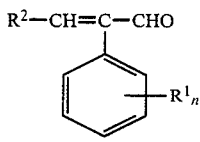   I where $R^1$ is alkoxy, phenoxy, halogen, haloalkyl, haloalkoxy, haloalkylthiyl or nitro, n is an integer from 1 to 5, in the case of n being greater than 1 the $R^1$s being identical or different and in the event of nitro substitution the aromatic ring carrying not more than 3 nitro groups, and where $R^2$ is alkyl, cycloalkyl, unsubstituted or substituted aryl or hetaryl or a nonaromatic heterocyclic radical, which comprises reacting a phenylacetaldehyde of the general formula II

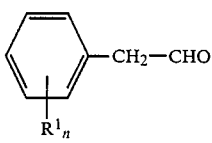   II with an aldehyde of the general formula III

[$R^2$–CHO]   III in the presence of a base and a solvent.

The invention further provides a novel α,β-substituted acrolein of the general formula Ia

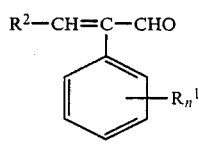   Ia where $R^1$ is halogen, $C_1$–$C_4$-alkoxy, phenoxy, $C_1$–$C_4$-haloalkyl, $C_1$–$C_4$-haloalkoxy or nitro, n is an integer from 1 to 5, in the case of n being greater than 1 the $R^1$s being identical or different and in the event of nitro substitution the aromatic ring carrying not more than 3 nitro groups, and where $R^2$ is a hetaromatic or nonaromatic heterocyclic radical containing from 1 to 3 nitrogen, oxygen and/or sulfur atoms.

The success of the novel process is surprising since it is known that the introduction of electron-withdrawing substituents $R^1$ in particular into compounds of the general formula II drastically increases the reactivity of the benzylic —$CH_2$— group, so that it was to be expected that the substituted phenylacetaldehyde would show a strong tendency to self-condensation.

For example, the crossed aldol condensation of 2-ethoxycarbonylmethoxyphenylacetaldehyde with benzaldehyde leads to a yield of only about 30% of the desired condensation product α-(2-methoxycarbonylmethoxyphenyl)cinnamaldehyde (DE-A 2,516,623).

Preferred starting materials II are compounds having electron-withdrawing substituents such as halogen atoms, eg. fluorine, chlorine or bromine, haloalkyl groups having for example from 1 to 10, in particular from 1 to 4, carbon atoms and from 1 to 3 halogen atoms, such as bromine, chlorine or fluorine, haloalkoxy groups or haloalkylthiyl groups having from 1 to 4 carbon atoms and from 1 to 3 of the halogen atoms mentioned. $R^1$ can be in addition $C_1$-$C_4$-alkoxy, phenoxy or nitro. The phenyl nucleus preferably carries 1, 2 or 3 substituents. Examples are the following compounds: 2-fluoro-, 3-fluoro-, 4-fluoro-, 2-chloro-, b 4-chloro-, 4-bromo-, 2,4-dichloro-, 2,4-difluoro-, 3,4-dichloro-, 2,6-dichloro-, 2,6-difluoro-, 2-chloro-6-fluoro-, 2-, 3- or 4-trifluoromethyl- and 4-trifluoromethoxyphenylacetaldehyde.

Suitable starting materials III are compounds where $R^2$ is straight-chain or branched alkyl, for example of from 1 to 10, in particular from 1 to 4, carbon atoms, cycloalkyl of 5 or 6 carbon atoms, substituted or unsubstituted aryl, eg. phenyl, p-biphenyl or naphthyl, possible substituents being halogen atoms, such as chlorine, bromine and/or fluorine, $C_1$-$C_4$-alkoxy, $C_1$-$C_4$-alkyl, phenoxy, nitro, $C_1$-$C_4$-haloalkyl and phenylsulfonyl, or is hetaryl, in particular having from 1 to 3 hetero atoms, such as oxygen, sulfur and preferably nitrogen, or a saturated or unsaturated heterocyclic radical having 5 or 6 ring members and from 1 to 3, in particular 1, of the hetero atoms mentioned. Examples of $R^2$ are: methyl, ethyl, propyl, isopropyl, butyl, tert-butyl, cyclopentyl, cyclohexyl, 1-naphthyl, 2-naphthyl, p-biphenyl, phenyl, 2-chlorophenyl, 3-chlorophenyl, 4-chlorophenyl, 2-fluorophenyl, 3-fluorophenyl, 2-fluoro-6-chlorophenyl, 4-fluorophenyl, 4-bromophenyl, 2,4-dichlorophenyl, 3,4dichlohlorophenyl, 3,5-dichlorophenyl, 2,6-dichlorophenyl, -chloro-4-methylphenyl, 2-methoxyphenyl, 3-methoxyphenyl, 2,4-dimethoxyphenyl, 3,4-dimethoxyphenyl, 4-methoxyphenyl, 4-ethoxyphenyl, 4-tert-butoxyphenyl, 4-methylphenyl, 4-ethylphenyl, 4-isopropylphenyl, 4-tert-butylphenyl, 4-phenoxyphenyl, 3-phenoxyphenyl, 3-nitrophenyl, 4-nitrophenyl, 4-nitro-2-chlorophenyl, 3-trifluoromethylphenyl, 4-trifluoromethylphenyl and 4-phenylsulfonylphenyl, 2-, 3- or 4-pyridyl, 2-, 3- or 4-pyridazinyl, 2-pyrimidyl, 4-pyrimidyl, 2-thienyl, 3-thienyl, 2-furanyl, 3-pyranyl, 2-, 3- or 4-pyranyl, 2-, 3- or 4-thiopyranyl, 2-, 4- or 5-oxazolyl, 2-, 4- or 5-isooxazolyl and 3-piperidyl.

Important novel compounds I are in particular those shown in the Table in the contrast of the general method of preparation and also inter alia the following propenals:

2-(3,4-dichlorophenyl)-3-(3-pyridyl)propenal
2-(2,6-dichlorophenyl)-3-(3-pyridyl)propenal
2-(2-trifluoromethylphenyl)-3-(3-pyridyl)propenal
2-(3-trifluoromethylphenyl)-3-(3-pyridyl)propenal
2-(4-trifluoromethylphenyl)-3-(3-pyridyl)propenal
2-(4-trifluoromethoxyphenyl)-3-(3-pyridyl)propenal
2-(2-methyl-4-fluorophenyl)-3-(3-pyridyl)propenal
2-(2-chlorophenyl)-3-(3-pyridyl)propenal
2-(2-fluorophenyl)-3-(3-pyridyl)propenal
2-(3-fluorophenyl)-3-(3-pyridyl)propenal
2-(2,6-difluorophenyl)-3-(3-pyridyl)propenal
2-(2-chloro-6-fluorophenyl)-3-(3-pyridyl)propenal
2-(4-bromophenyl)-3-(3-pyridyl)propenal
2-(4-chlorophenyl)-3-(2-pyridyl)propenal
2-(4-fluorophenyl)-3-(2-pyridyl)propenal
2-(4-chlorophenyl)-3-(4-pyridyl)propenal
2-(4-fluorophenyl)-3-(4-pyridyl)propenal
2-(4-fluorophenyl)-3-(4-thiopyranyl)propenal
2-(4-fluorophenyl)-3-(2-thiopyranyl)propenal
2-(4-fluorophenyl)-3-(2-furanyl)propenal
2-(4-fluorophenyl)-3-(2-thienyl)propenal
2-(4-fluorophenyl)-3-(3-thienyl)propenal
2-(4-fluorophenyl)-3-(3-isoxazolyl)propenal
2-(4-fluorophenyl)-3-(4-isoxazolyl)propenal
2-(4-fluorophenyl)-3-(5-isoxazolyl)propenal
2-(4-fluorophenyl)-3-(2-oxazolyl)propenal
2-(4-fluorophenyl)-3-(4-oxazolyl)propenal
2-(4-fluorophenyl)-3-(5-oxazolyl)propenal
2-(4-fluorophenyl)-3-(2-thiazolyl)propenal
2-(4-fluorophenyl)-3-(2-pyrimidinyl)propenal
2-(4-fluorophenyl)-3-(4-pyrimidinyl)propenal
2-(4-fluorophenyl)-3-(3-pyridazinyl)propenal
2-(4-fluorophenyl)-3-(4-pyridazinyl)propenal
2-(4-fluorophenyl)-3-(3-pyrazinyl)propenal.

The reaction of the starting materials II and III is carried out in the presence of bases which are customary in aldol condensations.

Suitable bases are for example alkali metal and alkaline earth metal hydroxides, eg. sodium hydroxide, potassium hydroxide, lithium hydroxide, barium hydroxide and calcium hydroxide, alkali metal and alkaline earth metal carbonates, e.g. sodium carbonate, potassium carbonate, lithium carbonate and calcium carbonate, or alkoholates, eg. sodium or potassium methylate, ethylate, propylate, isopropylate, n-butanolate, isobutanolate, tert-butanolate or cyclohexanolate, and also primary and secondary amines, eg. piperidine, pyrrolidine or diisopropylamine.

The amount of base is in general from 0.01 to 1, in particular from 0.01 to 0.5, mole per mole of starting material II.

The ratio of starting material II:III can be from 1, to 0.1 in particular from 1 to 0.5. In order to avoid side reactions, equimolar amounts are frequently advantageous.

The reaction of II with III can be carried out in the absence or preferably in the presence of a solvent which is inert under the reaction conditions. Examples of suitable solvents are ethers, such as methyl tert-butyl ether, tetrahydrofuran, dimethoxyethane or dioxane, amides, eg. dimethylformamide, dimethylacetamide or N-methylpyrrolidone, and urea derivatives, eg. N,N'-dimethylpropyleneurea (DMPU) or N,N-dimethylethyleneurea (DMEU). Hydrocarbons or halohydrocarbons, eg. pentane, hexane, heptane, cyclohexane, toluene, xylene, dichloromethane, trichloromethane, tetrachloromethane, dichloroethane or chlorobenzene, and in particular low molecular weight alcohols, eg. methanol, ethanol, isopropanol, n-propanol, n-butanol, isobutanol, tert-butanol or cyclohexanol, are particularly suitable. The best yields are obtained using methanol or a methanol/water mixture as the solvent.

The amount of solvent is in general 100–300 ml/mol.

The reaction can be carried out at −20° C. to +120° C., preferably from −5° C. to +60° C., particularly preferably from 0° C. to 40° C., under atmospheric or superatmospheric pressure, continuously or batchwise using conventional techniques.

Advantageously the reaction is carried out by initially taking the aldehyde III in a solvent together with the desired base and metering in the phenylacetaldehyde II, or by initially taking the base with the solvent at the reaction temperature and adding the appropriate mixture of phenylacetaldehyde (aldehyde II) and aldehyde III.

On completion of the reaction the end product can be isolated in a conventional manner, for example by extracting with a suitable organic solvent eg. chlorohydrocarbons, hydrocarbons, esters, ethers or particularly preferably by direct crystallization from the reaction mixture.

The products of the formula I can be formed as E- or Z-isomers. The isomer mixture can be resolved in a conventional manner, for example on the basis of solubility differences between the isomers or by column chromatography, and the isomers isolated in pure form. In the synthesis of the novel compounds listed below the isomer mixture obtained contains in most cases predominantly the E-isomer in a proportion of 90-99%.

The acroleins I which are obtainable by the process according to the invention are used in preparing hydroxymethyloxiranes which are useful intermediates in the synthesis of antimycotic and fungicidal azolylmethyloxiranes. Azolylmethyloxiranes of this type are described in EP-A 94, 564. The conversion of acroleins I into hydroxymethyloxiranes can be carried out according to the method given in the earlier patent application DE-A 3,601,927, by epoxidation to give formyloxiranes and subsequent reduction.

EXAMPLE

General method of preparation 0.1 mol of NaOH was dissolved in 250 ml of methanol, and 1.1 mol of aldehyde III were added dropwise whilst cooling with ice. 1 mol of phenylacetaldehyde II was then added dropwise at 20°–30° C. in the course of from about 4 to 5 hours. After about 30 minutes the pH was adjusted to 7 with 10% strength $H_2SO_4$. After evaporating off the solvent under reduced pressure the remaining reaction mixture was subjected to fractional distillation.

Starting materials and physical data of the products are given in the Table below.

TABLE

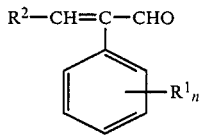

| Exp. | $R_n^1$ | $R^2$ | Yield of I % | Boiling point of I mbar/°C. |
|---|---|---|---|---|
| 1 | H | 3-pyridyl | 86 | 0.6/160 (mp. 94° C.) |
| 2 | 4-fluoro | 3-pyridyl | 85 | 0.6/153–156 |
| 3 | 2,4-dichloro | 3-pyridyl | 91 | 0.5/167 |
| 4 | 2,4-difluoro | 3-pyridyl | 85 | 0.5/150 |
| 5 | 3,4-difluoro | 3-pyridyl | 87 | 0.5/150 |
| 6 | 4-chloro | 3-pyridyl | 91 | 0.5/163 |
| 7 | H | 4-pyridyl | 81 | 0.35/160 |
| 8 | 4-fluoro | 4-pyranyl | 94 | 0.3/142 |
| 9 | 4-chloro | 4-pyranyl | 94 | 0.3/148 |
| 10 | 4-fluoro | 3-pyranyl | 96 | 0.3/130 |
| 11 | 4-fluoro | 2-pyranyl | 92 | 0.3/138 |
| 12 | 4-fluoro | 3-thiopyranyl | 91 | 0.3/142 |
| 13 | 4-fluoro | n-butyl | 81 | 0.1/88–91 |
| 14 | 4-fluoro | 2-chlorophenyl | 93 | 88–92 (mp.) |

We claim:

1. An α-β-substituted acrolein of the formula where $R^1$ is halogen, $C_1$–$C_4$-alkoxy, phenoxy, $C_1$–$C_4$-haloalkyl, $C_1$–$C_4$-haloalkoxy or nitro, n is an integer from 1 to 5, in the case of n being greater than 1 the $R^1$s being identical or different and in the event of nitro substitution the aromatic ring carrying not more than 3 nitro groups, and where $R^2$ is 2-pyridyl, 3-pyridyl or 4-pyridyl.

2. An α-β-substituted acrolein as claimed in claim 1, where $R^1$ is halogen, $C_1$- to $C_4$-haloalkyl or $C_1$- to $C_4$-haloalkoxy and n is an integer from 1 to 3.

3. An α-β-substituted acrolein as claimed in claim 1, wherein $R_y2$ is 3-pyridyl.

4. An α-β-substituted acrolein as claimed in claim 2, wherein $R_2$ is 3-pyridyl.

* * * * *